United States Patent [19]

Banko

[11] 4,167,943
[45] Sep. 18, 1979

[54] BLADE TYPE ROTATABLE SURGICAL CUTTING INSTRUMENT WITH IMPROVED CUTTER BLADE WEAR

[75] Inventor: Anton Banko, Bronx, N.Y.

[73] Assignee: Surgical Design Corp., Long Island City, N.Y.

[21] Appl. No.: 810,495

[22] Filed: Jun. 27, 1977

[51] Int. Cl.² ............................................. A61B 17/32
[52] U.S. Cl. ................................... 128/305; 128/752; 128/6; 128/276
[58] Field of Search .................. 128/305, 276, 2 B, 6; 30/240, 133, 41.5

[56] References Cited

U.S. PATENT DOCUMENTS

| | | | |
|---|---|---|---|
| 3,732,858 | 5/1973 | Banko | 128/2 B |
| 3,945,375 | 3/1976 | Banko | 128/6 |

Primary Examiner—Robert W. Michell
Assistant Examiner—Michael H. Thaler
Attorney, Agent, or Firm—Darby & Darby

[57] ABSTRACT

A cutter body for a surgical instrument having at least one blade surface thereon which rotates relative to a fixed blade surface. The cutter body and the rotatable blade are shaped to minimize the stress and wear of the rotatable cutter blade.

11 Claims, 9 Drawing Figures

BLADE TYPE ROTATABLE SURGICAL CUTTING INSTRUMENT WITH IMPROVED CUTTER BLADE WEAR

In my prior U.S. Pat. No. 3,945,375 granted Mar. 23, 1976, as well as the various patents referred to therein, a surgical instrument is disclosed of the type having a rotating cutter with a blade which moves relative to a stationary cutting surface to produce a shearing action. In my prior U.S. Pat. No. 3,732,858 granted May 15, 1973 a surgical instrument is disclosed having a blade type cutter which operates without a stationary blade to cut or chap away pieces of the object being cut. The instruments are disclosed in both patents as being used for microsurgery applications, such as operating in or on the eye, where they are to be inserted into the eye to remove tissue from a body.

The rotating portion of the cutter of U.S. Pat. No. 3,945,375 is of generally trunco-conical shape and formed with a pair of helical cutting flutes spaced 180° apart. Each flute has a cutting blade surface. The rotatable cutter is mounted at the end of a shaft which is urged forward in the tip of the instrument by the force of a spring. There is a zero clearance between the inside of the tip and the blades so that the net result is a controlled self-sharpening action as the blades wear and are moved forward in the tip.

The rotating cutter of FIGS. 7-9 of U.S. Pat. No. 3,732,858 is a double sided blade which is mounted on the end of a shaft. A cut is made every 180° of the shaft rotation.

The present invention is directed to improvements in cutters for the aforementioned types of instruments and particularly those of the general type shown in FIGS. 7-9 of my U.S. Pat. No. 3,732,858. In accordance with the invention, a generally trunco-conical cutter body is provided with a pair of double edged blades thereon which are spaced 180° apart on center. The surface of the blades decreases in width from the rear of the cutter body, where the cutting body is supported, toward its front, where the active cutting area is located. This arrangement provides a stress distribution thereby controlling and reducing the wear at the active cutting area. The arrangement also permits locating the active cutting area closer to the tip of the instrument.

It is therefore an object of the present invention to provide an instrument for removing tissue from a portion of a body.

An additional object is to provide an instrument for removing material from a body in which a probe is to be inserted into the body, the instrument including a rotatable bladed cutter.

Another object is to provide an instrument for removing tissue from a body in which the instrument brings tissue into a cutting relationship with a rotatable cutter.

A further object is to provide an instrument with a rotatable cutter blade in which blade wear is minimized and controlled.

An additional object is to provide a cutter body for an instrument having a blade supporting region and a cutting region in which the width of the blade decreases from the supporting to the cutting region.

Another object is to provide a cutter body for an instrument having a supporting region and a cutting region in which a portion of the body is adapted for controlled wear.

Other objects and advantages of the present invention will become more apparent upon reference to the following specification and annexed drawings, in which.

Figure 3:
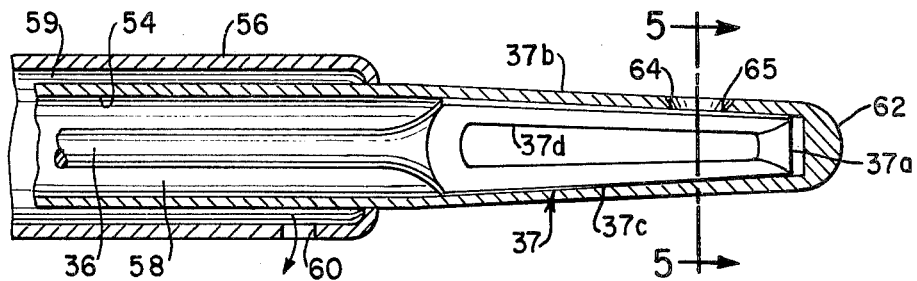
FIG. 3 is an elevational view partly in section showing the front end of the instrument.
Figure 4:
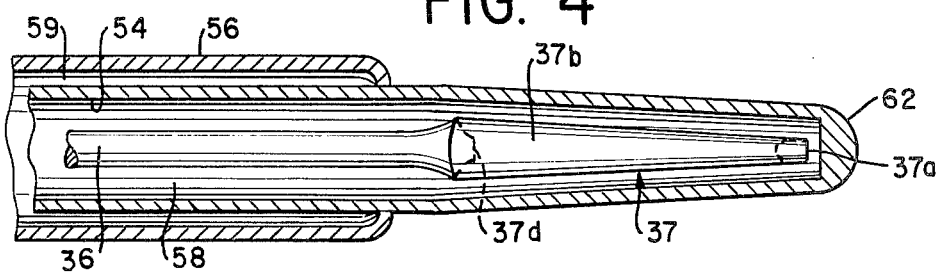
FIG. 4 is a view similar to FIG. 3 showing the cutter body turned by 90°.
Figure 5:
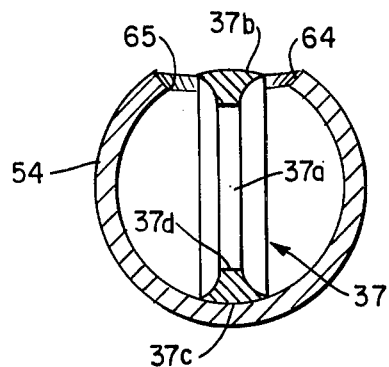
Figure 6:
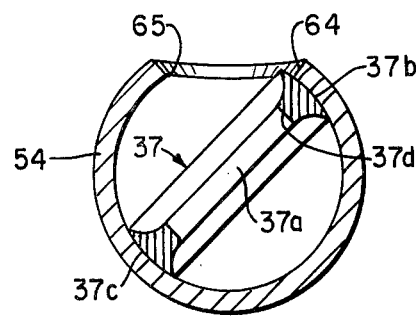
Figure 7:
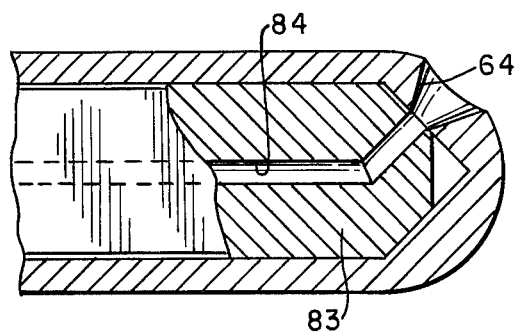
Figure 8A:
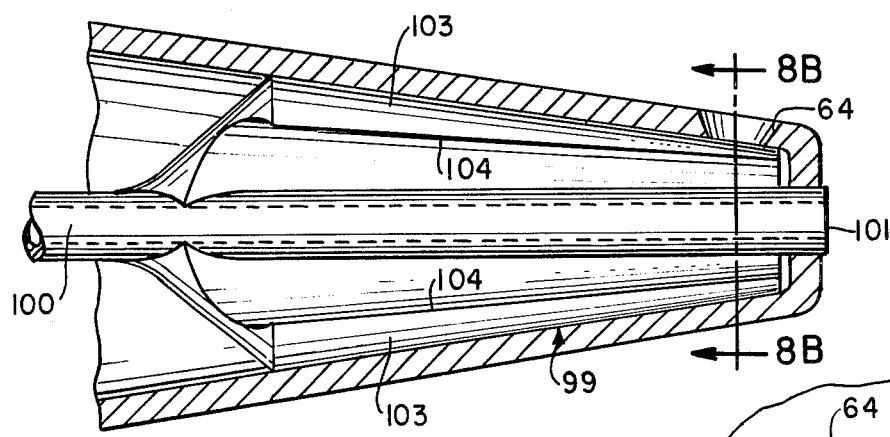
Figure 8B:
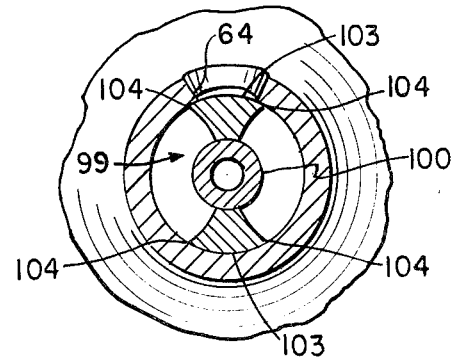

FIGS. 5 and 6 are cross-sectional views taken along lines 5—5 and 6—6 of FIGS. 3 and 4 respectively;

FIG. 7 is a fragmentary view, partly in cross-section, of the tip of a further embodiment of the invention;

FIG. 8A is a view partly in cross-section of another type of cutter blade according to the invention; and FIG. 8B is a cross-sectional view taken along lines 8B—8B of FIG. 8A.

Figure 1:
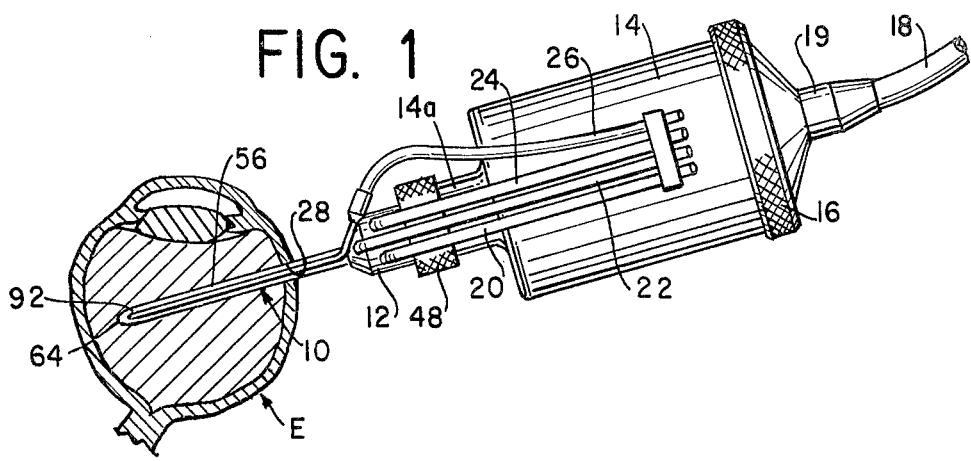
FIG. 1 is an overall plan view of the instrument shown for use in performing an operation in the eye.

Referring to FIG. 1, the instrument includes a probe extending from a fluid supply cup 12 which in turn is attached to a motor housing 14. The housing 14 contains a conventional electric motor (not shown) and is closed off by a cap 16 which is threaded and otherwise sealed to the main housing 14. Cable 18 extends through a grommet 19 in the cap 16 to supply current to the motor. A suitable switching circuit (not shown) for the motor can be provided at a location remote from the instrument.

Extending outside the housing, and attached to the housing if desired, are three fluid flow conduits 20, 22 and 24. These conduits respectively provide evacuation pressure, irrigation fluid and a reverse flow fluid through cup 12 to the probe 10 in a manner to be described. An optical rod, or bundle of optic fibers 26 is also shown attached to the probe 10.

The probe 10 is shown in FIG. 1 inserted through an opening 28 in the eye E. The probe 10 has located therein a cutter (not shown in FIG. 1) which is adapted to cut tissue from within the eye. The cut tissue is removed via the evacuation conduit 20. It should be understood, of course, that the instrument can be used at any body location of a human or animal.

Figure 2:
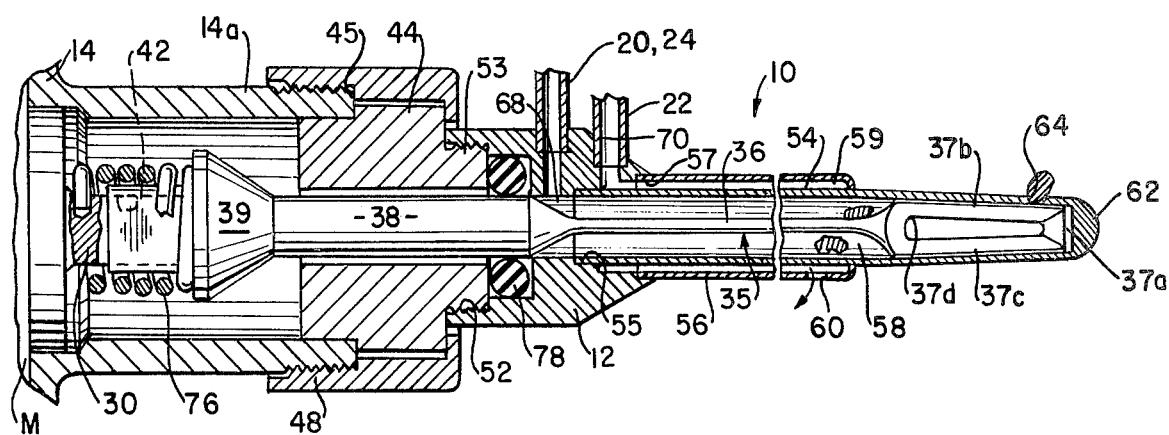
FIG. 2 is a cross-sectional view of a portion of the instrument showing the details thereof.

FIG. 2 shows the details of the instrument. The motor housing 14 contains the motor M which has an output shaft 30 extending into a neck 14a on the housing. The instrument has a cutting tool 35 which includes a shaft 36, a cutter 37, and a shank 38 whose end is fastened to a holder 39 having a shoulder 40. Holder 39 has a partial internal bore 42 which fits over the motor shaft 30.

The cutting tool shank 38 fits in a bushing 44 having a shoulder 45 which is held against the end of neck 14a by a collar 48 threaded onto housing neck 14a.

The fluid supply cup 12 is threaded at 52 onto a shoulder 53 on bushing 44. A pair of tubular shells 54 and 56 are mounted on internal steps 55 and 57 on the front end of the cup 12. Inner shell 54 defines a central flow passage for evacuation force and reverse fluid flow while the space between shells 54 and 56 defines a passage 59 for the flow of irrigation fluid. The irrigation fluid exits through an opening 60 located near the end of the outer shell 56.

The front end of shell 54 is sealed off by a nose cone 62 of truncated conical shape. Outer shell 56 has its end sealed off on inner shell 54. Outer shell 56 can be extended further from the portion shown. The shells 54, 56 and the cone 62 are made of a suitable biologically inert metal material, such as stainless steel, so the parts can be welded to each other. The nose cone 62 has an opening 64 at a selected position along its length. The opening 64 is of generally circular shape and has an inwardly tapering wall 65. The lower edge of wall 65 is sharpened to form a cutting edge. Opening 64 is preferably disposed 180° from the irrigation fluid opening 60 although any other suitable spacing can be used.

Cup 12 is formed with a first stepped bore 68 into which the fluids from both conduits 20 and 24 are applied. It is preferred that the two conduits 20 and 24 be connected together internal to probe 10 in the area of cap 12 and a common outlet conduit inserted in bore 68. The outlet of the bore 68 communicates with the interior passage 58 of the probe so that the passage can receive both suction and reverse flow-fluids. Similarly, cup 12 is formed with a second bore 70 to accept and hold the irrigation fluid conduit 22. The bore 70 communicates with the passage 59 between shells 54 and 56 and the fluid exits out of the outlet opening 60.

The evacuation force for conduit 20 is produced by any suitable means. A constant displacement type pump can be used to produce the evacuation. The irrigation fluid for conduit 22 and the reverse flow fluid for conduit 24 are preferably sterile solutions, for example, saline solutions of the same or different salinity.

The cutter 37 of cutting tool 35 is urged toward the inner surface of the front end of the nose cone 62 by a spring 76 which acts between the end of the motor 14 and the shoulder 40 of key 39. Thus, a force is always exerted forwardly and longitudinally of the axis of tool 35. An O-ring 78 is placed over shank 38 in cup 12 between a shoulder of the cup terminating the passage through which the cutter extends and the bushing neck 53. This seals off fluid between bore 68 and the motor housing 14, and the atmosphere.

The cutter tool shaft 36 between the shank 38 and the cutter 37 is preferably of a material which has some degree of flexibility or elasticity. For example, it has been found that stainless steel is a satisfactory material having a dimension, for example, of 0.022 inch. The flexibility of shaft 36 and the use of spring 76 urges the cutter 37 into engagement with the inner surface of cone 62 over a portion of the cutter body. This is described below.

The cutter 37 can also be formed of the same, or similar material as the shaft 36. If desired, the complete cutting tool 35 can be milled or otherwise suitably formed of a single piece of material.

The cutter 37 is formed with two double edged blades 37b and 37c and a hollow central section 37d. The blades 37b, 37c are sections of a truncated cone whose outer periphery corresponds to and has a zero clearance engagement with the inner surface of nose cone 62. The proposed advantages of this particular block configuration is described in detail below. The blades 37b, 37c are spaced 180° apart on center and occupy about 30°-60° of a circle. While two blades 37b, 37c are shown, there can be only one blade or there can be three or more. A symmetrical spacing is preferred to achieve better balance. The principal requirement of the blades 37b, 37c is that they extend in front of and in back of the opening 64 during a complete cycle of rotation of tool 35 so that there always will be engagement of the blade surfaces of 37b with the cutting surface of the wall 65 surrounding the opening 64.

The operation of the instrument proceeds as follows. An incision is first made in the portion of the body into which the probe is inserted. The probe is then inserted through the opening. The motor 14 is operated to energize the cutter tool 35 to cause the blades of cutter 37 to rotate with respect to the shearing edges 65 of the opening 64.

Evacuation force is applied through conduit 20 and the central passage to draw tissue into the opening 64. As the cutter 37 rotates, the blades sweep across the opening 64. The outer diameter of blades of cutter 37 and the inner diameter of the nose cone are such that the edges of the blades extend into the opening 64 as they sweep by. The spring 76 urges the tool 35 forward. The tissue caught between the edge of each cutter blade and the wall 65 of the opening 64 is carried along with the rotation of the blade until there is a shearing cut made between the blade edge and the wall. In this way, tissue is cut each time a blade passes under the opening 64 during each rotation of the tool 35.

The particles of tissue cut off and any fluid removed from the operating field are moved down the central passage 58 out through the conduit 20 into a collecting receptacle (not shown).

Irrigating fluid can be supplied from the conduit 22 through the outer passage 59 and out the opening 60. This can be done at the same time the tissue is being cut and removed from the operating field. The irrigating fluid can serve several functions. First of all, it can be supplied to an enclosed operating field, such as the eye, to compensate for removed fluid and tissue. This prevents the eye from collapsing. In addition, the irrigation fluid can be used to wash away or to position tissue within the operating field by suitably rotating the instrument. It also serves as a transporting means forming a suspension with the separated material.

A reverse flow fluid can be supplied through the conduit 24 into the central passage 58. It is sometimes desired to use this fluid to move particles which may have been trapped in the central passage 58 or in the drill flutes 37b. One type of fluid control system for the suction, irrigation and reverse fluid flows is described in my copending application Ser. No. 208,282, filed Dec. 15. 1971, Now U.S. Pat. No. 3,812,855 dated May 28, 1974, entitled "System for Controlling Fluid and Suction Pressure", which is assigned to the same assignee.

In the instrument shown in FIG. 2 of U.S. Pat. No. 3,945,375, a space is provided between the front end of the barrelshaped cutter and the front end of the instrument tip. In that instrument, after a while the fluted cutter blades wear down and, due to the spring biasing of the shaft, the cutter is moved forward towards the end of the tip. When the cutter is worn down to a point where the space is filled by the cutter body, a problem is then encountered in that the cutter body tilts or cocks causing the back portion of the body to contact the inner surface of the tip at a point. Stresses above the elastic limit of the cutter body material are produced and the structure is rapidly worn away or collapses. There is also excessive wear between the surface of the rotating blade and the inner surface of the evacuation port which forms the stationary cutting surface. This excessive wear creates a gap between the two shearing surfaces thereby making the cutting less efficient and eventually impossible.

The cutter of FIGS. 7-9 of U.S. Pat. No. 3,732,858, does not suffer from the wear problem since it does not have a rotating blade which turns against a stationary surface. However, when a stationary surface is provided, such as shown in FIGS. 3-4, the problem is encountered. In the cutter of FIGS. 7-9 of U.S. Pat. No. 3,732,858 the edges of the blades have a constant width (surface area) throughout their entire length, that is, over the entire length of the cutter body. In accordance with the subject invention, the width of the rotating cutter blades 37b, 37c varies from back to front of the cutter body. For reasons given below, this aids in controlling the wear problem. More particularly, as shown in FIG. 3, the blades 37b, 37c are sections of a truncated cone with the surface area of each blade 37b, decreasing going from the back (left) to the tip (right) of the cutter body. The amount of decrease in blade width (surface area) from maximum to minimum depends on the change in force normal to the surface of the blade that is required. In the embodiment of FIGS. 3–6, it is approximately about fifty percent. The percentage ratio can be virtually infinite if the tip of the cutter body comes to a point or is very small. As described before, each blade 37b, 37c is double-edged.

By providing the larger surface area at the rear end of each blade, a greater surface area is available for supporting the cutter body. Also, since there is a greater surface area, the amount of stress is decreased and with it the wear.

In general, it can be said that the wear of each cutter blade is a function of friction times the velocity of rotation of the cutter body times the stress. That is:

Wear=$\mu$(coefficient of friction)$\ominus$V (velocity)$\times\delta$(stress)

The larger diameter portion of the blade has a higher peripheral velocity. Stress is inversely proportional to the area of blade surface contact. By increasing the area of the supporting surface, the stress on the supporting area of the blade is decreased and, therefore, assuming the same amount of friction and time, the total wearing is decreased.

The use of the variable surface area blade provides a further advantage in that it reduces the travelling space needed between the end of the cutter body and the front of the instrument tip. In the embodiment of FIGS. 3-6, the tip 37a of the cutter is flat and there is a small space between this tip and the inner surface 67 of the probe which is shown as being pointed to correspond to a drilled hole but which also can be flat or rounded. For cutting action it is only necessary that the end 37a of the cutter extend under the edge 65 of the port 64. The front end 37a of the cutter can be brought very close to the end 67 of the probe.

Since the requirement for travelling space on the tip is reduced, this means that the evacuation port 64 can be moved closer to the end of the tip of the instrument. In many cases, this is considered to be an advantage by a surgeon conducting an operation.

In practice it has been found that the travelling space at the end of the instrument tip can be virtually eliminated if the varying surface area blade surface is provided so that the front end of the cutter body can make essentially a point contact with the inner surface of the instrument tip in the area in front of the stationary blade 64 at the evacuation port 65. This is so because with the reduced amount of blade contact surface area at the front end of the tip, there is a controlled amount of wear at the front end 37a of the cutter body. That is, as explained above, wear is a function of velocity. If a pointed tip is used the peripheral velocity at the front end of the cutter body is relatively low, since the radius of the body there is small. There is basically a surface contact at the front end of the body which is a point, or small circular area, describing a circle of relatively small radius. The contact area should be such that the elastic limits of the cutter body are normally not exceeded. If and when this occurs, the blade portion is subjected to excess stress and would collapse. If the tip 37a of the body wears, the body is pushed further forward toward the instrument tip end to an area where the blade surface area contact is wider thereby providing support and continuous contact with the shearing surfce 65 surrounding the evtacuation port 64. Utilizing this arrangement the evacuation port can be brought out substantially almost to the end of the instrument tip but above the center line so that there can be a shearing action.

FIG. 7 shows a further embodiment of the invention. Here, a solid trunco-conical cutter body 83 is provided which fits in a generally conical front end portion 90 of the probe tip. Body 83 has a passage 84 therethrough for evacuation of severed material. The passage 84 terminates in a hole 85. The body 83 is either rotated or oscillated back and forth. Cutting action is obtained for the material entering the port 64 each time the portion of the body 83 surrounding hole 84 sweeps across the port 64. In a prior version of the instrument of FIG. 7, the body 83 was conical and extended out to fill the space 90 at the probe tip. Thus, body 83 was more or less supported at the tip area of its cone. This was at a point where the velocity and consequent wear is minimal. The portions of the conical body, where the hole 84 is located had a greater velocity and wear resulting in a gap being produced between the rotating edge surrounding hole 64 and the stationary edge 64 of the port with the consequence that cutting was impaired or closed entirely. The area of the conical body surrounding the hole 84 was subjected to similar wear resulting in the cone being able to tilt about its apex.

In accordance with the present invention, the foregoing problem is greatly reduced, and in some cases eliminates, by removing the point of support at the apex of the cone which was used in prior art instruments. That is, the cone is truncated as shown at 87. The removal of the apex of the cone provides a space into which the rotating portion of the cone move when wearing occurs.

By truncating the conical cutter body 83, its supporting surface area is increased. That is, the stress is now taken up by the wider diameter wall portion of the cutter body closest to its base rather than by the apex area. This aids in controlling the wearing action of the cutter and increases its useful life.

FIGS. 8A and 8B show another embodiment of the invention used in conjunction with a so-called side cutter blade. The cutter body 99 is attached to a hollow tubular member 100 which extends through an opening 101 in the front of the probe and through which the infusion fluid is ejected. The rear part of the tubular member 100 serves as the shaft and it can be spring biased as in FIGS. 1-3. The cutter body 99 is tapered becoming narrower toward the front of the probe. Cutter body 99 is formed with two opposed rounded extending surfaces 103 having a cutting edge 104 on each end. Surfaces 103 are shaped to rotate within the probe. As seen, body 99 is generally frustro-conical and each of the surfaces 103 is a sector of the frustro-conical body.

Surfaces 103 are of decreasing width from the back, or shaft end, of the cutter body 99 to the front end. The cutter body is urged forward so that there is minimum clearance between it and the inner surfce of the probe. The tube 100 is rotated moving the cutter body across the port 64. Each time an edge 104 of the body crosses the port, it shears the material trapped between it and the surrounding port edge. An oscillating motion is also usually provided for a cutter of this general type.

The increase of the areas of surfaces 103 from their front to their back has the same general function and achieves many of the advantages of the variable width supporting blades of FIGS. 1-6. That is, there is a larger support surface at the back and a reduced velocity and stress at the front. This aids in controlling the wear of the cutter. While a space is shown between the front of the cutter body and the front end of the probe, it should be understood that there can be contact by modifying the shape of the front end of the cutter body and of the probe to have complementary conical or curved surfaces so that there is a relatively small area of surface contact at the front of the cutter body. This is described in greater detail in my copending application Ser. No. 810,399 filed June 27, 1977 concurrently herewith and entitled "Rotatable Surgical Cutting Instrument With Improved Cutter Blade Wear".

In a prior art cutter of this type, the body was made generally cylindrical and the width of the surfaces on which the blades were formed was the same from the front to the back of the cutter body. In such a cutter body the gap between the blade edges and the cutting port 64 increased with wear and the wearing action could not be controlled since the front of the cutter body was subjected to at least the same velocity and stress as the rear of the body. In the embodiment of FIG. 8 a continuous nogap engagement and better wearing control can be obtained in view of the stress distribution and the reduced peripheral velocity of the cutter body at its front end where the cutting takes place.

What is claimed is:

1. A surgical instrument for cutting tissue comprising a first tubular member having a tapered end portion, said first tubular member formed with an opening therein for the tissue to enter to be cut, said first tubular member also formed with a shearing surface around at least a portion of the opening, a cutting tool within said tubular member, said cutting tool including a shaft having a cutter at one end and said cutter having a body which is tapered with a first taper complementary to the tapered end portion of said first tubular member, said body having at least one cutting surface formed thereon, means engaging said shaft for turning said cutting tool, means for bringing the cutting surface of the cutter body into positive engagement with the inner surface of said tubular member in the area of said shearing surface, said cutter body cutting surface and said opening shearing surface providing a shearing action on the tissue in said opening as the cutter cutting surface sweeps across the opening, said cutter body including at least one supporting surface, said supporting surface being at least a band extending straight and longitudinally of the cutter body along the direction of the shaft for engaging the inner surface of said tubular member and having a second taper such that said supporting surface increases in width going from said end of said first tubular member towards said shaft whereby the stress on the cutter body is controlled along its length.

2. A surgical instrument as in claim 1 wherein there is a space between the front end of said cutter body and the inner surface of of the front end of said first tubular member.

3. A surgical instrument as in claim 2 wherein the end of said cutter body supporting surface terminates beyond the shearing surface of the opening of said first tubular member which is closest to its front end.

4. A surgical instrument as in claim 1 wherein said means for bringing the cutter body into positive engagement with the inner surface of the first tubular member comprises means acting on said shaft in a direction longitudinal of said shaft for uring the cutter toward the end of said first tubular member.

5. A surgical instrument as in claim 1 wherein said cutter body supporting surface is at least a section of a truncated cone.

6. A surgical instrument as in claim 5 wherein said section of a truncated cone is a closed surface except for a hole formed therein, the edge of said hole forming said cutter body cutting surface.

7. A surgical instrument as in claim 1 wherein said cutter body is generally trunco-conical in shape, said cutter body supporting surface being a sector of the body of increasing width from the front end of the cutter toward the shaft, and edge of said sector forming said cutter body cutting surface.

8. A surgical instrument as in claim 7 wherein there are a pair of cutter body supporting surfaces spaced substantially 180° apart.

9. A surgical instrument as in claim 7 wherein the interior portion of the cutter body is hollowed out.

10. A surgical instrument as in claim 7 wherein said cutter body is mounted on said shaft, said shaft having a portion extending through the cutter body and said shaft portion being hollow.

11. A surgical instrument as in claim 1 wherein said cutter body support surface comprises a blade having at least one edge which comprises said cutter body cutting surface.

* * * * *